(12) United States Patent
Chalifour et al.

(10) Patent No.: US 7,060,670 B1
(45) Date of Patent: Jun. 13, 2006

(54) STEREOSELECTIVE ANTIFIBRILLOGENIC PEPTIDES AND PEPTIDOMIMETICS THEREOF

(75) Inventors: Robert Chalifour, Ile Bizard (CA); Francine Gervais, Ile Bizard (CA); Ajay Gupta, Pointe Claire (CA)

(73) Assignee: Neurochem (International) Limited, Lausanne (CH)

(*) Notice: Subject to any disclaimer, the term of this patent is extended or adjusted under 35 U.S.C. 154(b) by 0 days.

(21) Appl. No.: 10/009,122

(22) PCT Filed: May 4, 2000

(86) PCT No.: PCT/CA00/00515

§ 371 (c)(1),
(2), (4) Date: Jun. 18, 2002

(87) PCT Pub. No.: WO00/68263

PCT Pub. Date: Nov. 16, 2000

Related U.S. Application Data

(60) Provisional application No. 60/132,592, filed on May 5, 1999.

(51) Int. Cl.
*A61K 38/02* (2006.01)
*C07K 16/36* (2006.01)

(52) U.S. Cl. ............... 514/2; 514/7; 514/8; 530/328; 530/329; 530/300; 530/350; 436/9.1

(58) Field of Classification Search .......... 514/2, 514/17, 18, 7, 8; 530/300, 328, 329, 330, 530/350; 436/9.1
See application file for complete search history.

(56) References Cited

U.S. PATENT DOCUMENTS

| | | | |
|---|---|---|---|
| 5,470,951 A * | 11/1995 | Roberts .................... 530/330 |
| 5,514,548 A | 5/1996 | Krebber et al. |
| 5,578,451 A | 11/1996 | Nishimoto |
| 5,652,334 A | 7/1997 | Roberts |
| 5,688,651 A | 11/1997 | Solomon |
| 5,721,130 A | 2/1998 | Seubert et al. |
| 5,753,624 A | 5/1998 | McMichael et al. |
| 5,817,626 A | 10/1998 | Findeis et al. |
| 5,837,672 A | 11/1998 | Schenk et al. |
| 5,851,996 A | 12/1998 | Kline |
| 5,854,204 A | 12/1998 | Findeis et al. |
| 5,854,215 A | 12/1998 | Findeis et al. |
| 5,869,093 A | 2/1999 | Weiner et al. |
| 5,891,991 A | 4/1999 | Wasco et al. |
| 5,985,242 A * | 11/1999 | Findeis et al. ............. 424/9.1 |
| 6,261,569 B1 | 7/2001 | Comis et al. |
| 6,277,826 B1 * | 8/2001 | Findeis et al. ............. 514/17 |
| 6,303,567 B1 * | 10/2001 | Findeis et al. ............. 514/2 |
| 6,319,498 B1 | 11/2001 | Findeis et al. |
| 6,331,440 B1 * | 12/2001 | Nordstedt et al. .......... 436/501 |
| 6,610,658 B1 * | 8/2003 | Findeis et al. ............. 514/17 |
| 6,670,399 B1 * | 12/2003 | Green et al. ............... 514/578 |
| 6,689,752 B1 * | 2/2004 | Findeis et al. ............. 514/16 |
| 6,831,066 B1 * | 12/2004 | Findeis et al. ............. 514/17 |

FOREIGN PATENT DOCUMENTS

| | | |
|---|---|---|
| EP | 0 584 452 A1 | 3/1994 |
| EP | 0 752 886 B1 | 1/1997 |
| WO | WO 94/05311 | 3/1994 |
| WO | WO 94/14836 | 7/1994 |
| WO | WO 94/19692 | 9/1994 |
| WO | WO 95/05393 | 2/1995 |
| WO | WO 95/05849 | 3/1995 |
| WO | WO 95/08999 | 4/1995 |
| WO | WO 95/12815 | 5/1995 |
| WO | WO 95/23166 | 8/1995 |
| WO | WO 95/31996 | 11/1995 |
| WO | WO 96/13583 | 5/1996 |
| WO | WO 96/28471 | 9/1996 |
| WO | WO 96/34887 | 11/1996 |
| WO | WO 96/37621 | 11/1996 |
| WO | WO 97/08320 | 3/1997 |
| WO | WO 97/21728 * | 6/1997 |
| WO | WO 9721728 * | 6/1997 |
| WO | WO 97/32017 | 9/1997 |
| WO | WO 98/02462 | 1/1998 |
| WO | WO 98/05350 | 2/1998 |
| WO | WO 98/08868 | 3/1998 |
| WO | WO 98/22120 | 5/1998 |
| WO | WO 99/10374 * | 3/1999 |
| WO | WO 99/27944 | 6/1999 |
| WO | WO 99/27949 | 6/1999 |
| WO | WO 99/58564 | 11/1999 |
| WO | WO 99/60021 | 11/1999 |
| WO | WO 99/60024 | 11/1999 |

(Continued)

OTHER PUBLICATIONS

Thompson, K. H. et al. (1999) Vanadium compounds as insulin mimics. Chem. Rev. vol. 99, pp. 2561-2571.*

(Continued)

*Primary Examiner*—Jon Weber
*Assistant Examiner*—Samuel Wei Liu
(74) *Attorney, Agent, or Firm*—Clark & Elbing LLP

(57) ABSTRACT

The present invention relates to antifibrillogenic agents for inhibiting amyloidosis and/or for cytoprotection for the treatment amyloidosis disorders. These agents include peptides, isomers thereof and peptidomimetic compounds thereof. These agents comprise peptide having a sequence identified from the glycosaminoglycan (GAG) binding region and the prot—prot interaction region of the amylo protein. The peptide has at least one [D] amino acid isomer substitution. The invention also relates to the peptide bound to a label for vivo imaging of amyloid deposits.

21 Claims, 7 Drawing Sheets

FOREIGN PATENT DOCUMENTS

| | | |
|---|---|---|
| WO | WO 00/20027 | 4/2000 |
| WO | WO 00/26238 | 5/2000 |
| WO | WO 00/43039 | 7/2000 |
| WO | WO 00/52048 A1 | 9/2000 |
| WO | WO 00/68263 | 11/2000 |

OTHER PUBLICATIONS

Pan, K.-M. et al. (1993) Conversion of alpha-helices into beta-sheets features in the formation of the scrapie prion proteins.☐☐Proc. Natl. Acad. Sci. U S A. vol. 90, pp. 10962-10966.*

Gasset, M. et al. (1993) Perturbation of the secondary structure of the scrapie prion protein under conditions that alter infectivity.☐☐Proc. Natl. Acad. Sci. U S A. vol. 90, pp. 1-5.*

Wong, B.-S. et al. (2001) Absence of protease-resistant prion protein in the cerebrospinal fluid of Creutzfeldt-Jakob disease. J. Pathol. vol. 194, pp. 9-14.*

Weher et al. (2004) Cytoprotective function of sAppalpha in human keratinocytes. Eur. J. Cell Biol. vol. 83, No. 11-12, pp. 701-708.*

Benkirane et al., "Antigenicity and Immunogenicity of Modified Synthetic Peptides Containing D-Amino Acid Residues," Journal of Biological Chemistry 258:26279-26285 (1998).

Findeis et al., "Modified-Peptide Inhibitors of Amyloid β-Peptide Polymerization," Biochemistry 38:6791-6800 (1999).

Flood et al., "Topography of a Binding Site for Small Amnestic Peptides Deduced from Structure-Activity Studies: Relation to Amnestic Effect of Amyloid β Protein," Proc. Natl. Acad. Sci. USA 91:380-384 (1994).

Giulian et al., "The HHQK Domain of β-Amyloid Provides a Structural Basis for the Immunopathology of Alzheimer's Disease," The Journal of Biological Chemistry 273:29719-29726 (1998).

Sela et al., "Different Roles of D-Amino Acids in Immune Phenomena," FASEB J., 11:449-456 (1997).

Tjernberg et al., "Arrest of β-Amyloid Fibril Formation by a Pentapeptide Ligand," Journal of Biological Chemistry 271:8545-8548 (1996).

Tjernberg et al., "Controlling Amyloid β-Peptide Fibril Formation with Protease-Stable Ligands," Journal of Biological Chemistry 272:12601-12605 (1997).

Tjernberg et al., "Controlling Amyloid β-Peptide Fibril Formation with Protease-Stable Ligands," Journal of Biological Chemistry 272:17894 (1997).

Torneiro et al., "Sequence-Selective Binding of Peptides in Water by a Synthetic Receptor Molecule," J. Am. Chem. Soc. 117:5887-5888 (1995).

Van Regenmortel et al., "D-peptides as Immunogens and Diagnostic Reagents," Current Opinion in Biotechnology 9:377-382 (1998).

* cited by examiner

STEREOSELECTIVE ANTIFIBRILLOGENIC PEPTIDES AND PEPTIDOMIMETICS THEREOF

This application is a U.S. national phase application under 35 U.S.C. § 371 of international application PCT/CA00/00515, filed May 4, 2000, which claims benefit of the filing date of U.S. provisional patent application No. 60/132,592, filed May 5, 1999 (now abandoned).

BACKGROUND OF THE INVENTION (a) Field of the Invention

The invention relates to agents having potent antifibrillogenic activity for the treatment of amyloidosis disorders and for imaging of amyloid deposits. These agents include peptides and peptidomimetic compounds thereof.

(b) Description of Prior Art

Amyloidosis refers to a pathological condition characterized by the presence of amyloid fibers. Amyloid is a generic term referring to a group of diverse but specific extracellular protein deposits that are seen in a number of different diseases. Though diverse in their occurrence, all amyloid deposits share common morphologic properties, stain with specific dyes (e.g. Congo red), and have a characteristic red-green birefringent appearance in polarized light after staining. They also share common ultrastructural, x-ray diffraction and infrared spectra features.

Some amyloidotic diseases can be idiopathic but most of these diseases appear as a complication of a previously existing disorder. For example, primary amyloidosis can appear without any other pathology or can follow plasma cell dyscrasia or multiple myeloma. Secondary amyloidosis is usually seen associated with chronic infection (such as tuberculosis) or chronic inflammation (such as rheumatoid arthritis). A familial form of secondary amyloidosis is also seen in Familial Mediterranean Fever (FMF). This familial type of amyloidosis, as one of the other types of familial amyloidosis, is genetically inherited and is found in specific population groups. Isolated forms of amyloidosis are those that tend to involve a single organ system. Different amyloids are also characterized by the type of protein present in the deposit. For example, neurodegenerative diseases such as scrapie, bovine spongiform encephalitis, Creutzfeldt-Jakob disease and the like are characterized by the appearance and accumulation of a protease-resistant form of a prion protein (referred to as AScr or PrP-27) in the central nervous system. Similarly, Alzheimer's disease, another neurodegenerative disorder, is characterized by congophilic cerebral angiopathy, neuritic plaques and neurofibrillary tangles. In this case, the plaque and blood vessel amyloid is formed by the deposition of fibrillar Aβ amyloid protein. In adult-onset diabetes, amyloids containing the IAPP amyloid protein accumulate in the pancreas. Other systemic diseases, complications of long-term hemodialysis and sequelae of long-standing inflammation or plasma cell dyscrasias are characterized by the accumulation of amyloids systemically. In each of these cases, a different amyloidogenic protein is involved in amyloid deposition.

Once these amyloids have formed, there is no known, widely accepted therapy or treatment that significantly dissolves the deposits in situ.

Each amyloidogenic protein has the ability to organize into β-sheet and to form insoluble fibrils that get deposited extracellularly. Each amyloidogenic protein, although different in amino acid sequence has the same property of forming fibrils and binding to other elements such as proteoglycan (glycosaminoglycan), amyloid P and complement component. Moreover, each amyloidogenic protein has amino acid sequences which, although different, will show similarities such as regions with the ability to bind to GAG's (referred to as the GAG binding site) as well as other regions which will promote β-sheet formation referred to as β-sheet region.

In specific cases, amyloidotic fibrils once deposited can become toxic to the surrounding cells. As per example, the Aβ fibrils organized as senile plaques have been shown to be associated with dead neuronal cells and microgliosis in patients with Alzheimer's disease. When tested in vitro, Aβ peptide was shown to be capable of triggering an activation process of the microglia (brain macrophages), which would explain the presence of microgliosis and brain inflammation found in the brain of patients with Alzheimer's disease.

In another type of amyloidosis seen in patients with Type II diabetes, the islet amyloidogenic protein, IAPP, has been shown to induce β-islet cell toxicity in vitro. Hence, appearance of IAPP fibrils in the pancreas of Type II diabetic patients could contribute to the loss of the β islet cells (Langerhans) and organ dysfunction.

Particularly, in patients with Alzheimer's Disease, an agent capable 1) of preventing amyloid fibril formation and deposition and 2) of directly or indirectly inhibiting Aβ-induced neurotoxicity and inflammation (microgliosis), could be a treatment of choice to prevent and arrest the development of Alzheimer's disease.

WO-A-9808868 concerns compounds that modulate natural beta-amyloid peptide aggregation. The compounds comprise a peptide, preferably based on a beta-amyloid peptide, that is comprised of 3–5 D-amino acid residues and includes at least two D-amino acid residues independently selected from the group consisting of D-leucine, D-phenylalanine and D-valine. In one embodiment the peptide is a retro-inverso isomer of a beta-amyloid peptide. In certain embodiments, the peptide is modified at the amino-terminus, the carboxy-terminus, or both.

It would be highly desirable to be provided with agents having potent antifibrillogenic activity for the treatment of amyloidosis disorders.

SUMMARY OF THE INVENTION

One aim of the present invention is to provide agents having potent antifibrillogenic activity for the treatment of amyloidosis disorders.

Another aim of the present invention is to provide a method for the treatment of amyloidosis disorders, such as Alzheimer's' disease.

A number of strategies for possible therapeutic intervention in amyloid development have been proposed. These strategies include reduction of the pool of precursor proteins, prevention of the interaction of precursor proteins and disruption of preformed amyloid. The present invention deals mainly with the second approach, prevention of precursor protein interactions. The ideal molecule to fulfill this function, would interact specifically with the amyloid protein and would in so doing prevent the protein from interacting with itself. When dealing with molecules that are chiral, it is standard practice to identify which of the stereoisomers possesses the activity, since in general, activity can be attributed to one or the other of the isomers. By using a stereochemically pure isomer, side reactions can be avoided or reduced.

In accordance with one embodiment of the present invention there is provided an antifibrillogenic agent for inhibiting amyloidosis and/or for cytoprotection, which comprises a peptide of Formula I, an isomer thereof, a retro or a retro-inverso isomer thereof or a peptidomimetic thereof:

$$Xaa_1\text{-}Xaa_2\text{-}Xaa_3\text{-}Xaa_4 \quad \text{I}$$

wherein, $Xaa_1$ is absent or selected from the group consisting of Lys, Lys-Lys, $Xaa_5$-Lys-, and Ala;

$Xaa_5$ is absent or selected from the group consisting of His-Gln-, His-His-Gln-, Val-His-His-Gln-, Glu-Val-His-His-Gln-, Asp-Asp-Asp-, Lys-Val-Asp-Asp-Gln-Asp-, Gln-;

$Xaa_2$ is absent or any amino acid;

$Xaa_3$ is absent, Val or Phe;

$Xaa_4$ is absent or selected from the group consisting of Phe, Phe-$NH_2$, Phe-Phe, Phe-Phe-Ala, Phe-Phe-Ala-$NH_2$, Phe-Phe-Ala-Gln, Phe-Phe-Ala-Gln-$NH_2$, Val-Leu-Lys, Val-Leu-Lys-$NH_2$;

wherein the peptide of formula I contains at least one Lys or Asp;

and wherein the peptide has at least one [D] amino acid residue, with the proviso that Lys-Lys-Leu-Val-Phe-Phe-Ala is an all-[D] peptide; and with the proviso that when $Xaa_5$ is Lys-Val-Asp-Asp-Gln-Asp- all of $Xaa_2$, $Xaa_3$, and $Xaa_4$ are absent.

Preferably, $Xaa_2$ is a hydrophobic amino acid residue such as a leucine residue.

In one embodiment of the invention, the peptide of formula I has at least two [D] amino acid residues, and more preferably at least three [D] amino acid residues. Optionally, the peptide of formula I has one [L] amino acid residue, or more preferably the peptide is an all-[D] isomer peptide.

In another embodiment of the invention, the peptide of Formula I is selected from the group consisting of:

| | |
|---|---|
| Lys-Ile-Val-Phe-Phe-Ala | (SEQ ID NO:1); |
| Lys-Lys-Leu-Val-Phe-Phe Ala | (SEQ ID NO:2); |
| Lys-Leu-Val-Phe-Phe-Ala | (SEQ ID NO:3); |
| Lys-Phe-Val-Phe-Phe-Ala | (SEQ ID NO:4); |
| Ala-Phe-Phe-Val-Leu-Lys | (SEQ ID NO:5); |
| Lys-Leu-Val-Phe | (SEQ ID NO:6); |
| Lys-Ala-Val-Phe-Phe-Ala | (SEQ ID NO:7); |
| Lys-Leu-Val-Phe-Phe | (SEQ ID NO:8); |
| Lys-Val-Val-Phe-Phe-Ala | (SEQ ID NO:9); |
| Lys-Ile-Val-Phe-Phe-Ala-$NH_2$ | (SEQ ID NO:10); |
| Lys-Leu-Val-Phe-Phe-Ala-$NH_2$ | (SEQ ID NO:11); |
| Lys-Phe-Val-Phe-Phe-Ala-$NH_2$ | (SEQ ID NO:12); |
| Ala-Phe-Phe-Val-Leu-Lys-$NH_2$ | (SEQ ID NO:13); |
| Lys-Leu-Val-Phe-$NH_2$ | (SEQ ID NO:14); |
| Lys-Ala-Val-Phe-Phe-Ala-$NH_2$ | (SEQ ID NO:15); |
| Lys-Leu-Val-Phe-Phe-$NH_2$ | (SEQ ID NO:16); |
| Lys-Val-Val-Phe-Phe-Ala-$NH_2$ | (SEQ ID NO:17); |
| Lys-Leu-Val-Phe-Phe-Ala-Gln | (SEQ ID NO:18); |
| Lys-Leu-Val-Phe-Phe-Ala-Gln-$NH_2$ | (SEQ ID NO:19); |
| His-His-Gln-Lys-Leu-Val-Phe-Phe-Ala-$NH_2$ | (SEQ ID NO:20); |
| Asp-Asp-Asp | (SEQ ID NO:21); |
| Lys-Val-Asp-Asp-Gln-Asp | (SEQ ID NO:22); |
| His-His-Gln-Lys and | (SEQ ID NO:23); |
| Gln-Lys-Leu-Val-Phe-Phe-$NH_2$ | (SEQ ID NO:24). |

More preferably, the peptide of formula I is a peptide as set forth in SEQ ID NO:2 or SEQ ID NO:3.

In accordance with one embodiment of the present invention there is provided a labeled conjugate for in vivo imaging of amyloid plaque, which comprises a conjugate of formula II:

$$A\text{-}B\text{-}C \quad \text{II}$$

wherein A is an amyloid plaque-targeting moiety selected from the group consisting of a peptide of Formula I as defined above, an isomer thereof, a retro or a retro-inverso isomer thereof and a peptidomimetic thereof, wherein B is a linker portion allowing attachment of the amyloid plaque-targeting moiety to C; and wherein C is a label that allows for in vivo imaging. Preferably, the linker portion B is selected from the group consisting of Glucose and Phe. Preferably, the label C is $^{99m}Tc$.

Still in accordance with the present invention, there is provided a method for the treatment of amyloidosis disorders in a patient, which comprises administering to the patient a therapeutically effective amount of a peptide of Formula I, or the antifibrillogenic agent, as defined above.

Further in accordance with the present invention, there is provided a composition for the treatment of amyloidosis disorders in a patient, which comprises a therapeutically effective amount of a peptide of Formula I, or of an antifibrillogenic agent, as defined above in association with a pharmaceutically acceptable carrier.

In accordance with the present invention, there is also provided a composition for in vivo imaging of amyloid plaques, which comprises a therapeutically effective amount of a labeled conjugate as defined above in association with a pharmaceutically acceptable carrier.

The peptide of Formula I or the antifibrillogenic agent may be used for inhibiting amyloidosis and/or for cytoprotection.

The labeled conjugate may be used for in vivo imaging of amyloid plaques.

The peptide of Formula I or the antifibrillogenic agent may alternatively be used for the manufacture of a medicament for inhibiting amyloidosis and/or for cytoprotection.

Similarly, the labeled conjugate may also be used for the manufacture of a medicament for in vivo imaging of amyloid plaques.

Other embodiments of these peptides include racemic mixtures and peptides having mixed chirality, i.e., different chirality at different chiral centers.

In accordance with the peptides Lys-Lys-Leu-Val-Phe-Phe-Ala (SEQ ID NO:2) and Lys-Leu-Val-Phe-Phe-Ala (SEQ ID NO:3), one stereoisomer, the D form, is found to be more active than the L form, and the D isomer is the preferred form for use of this peptide as a drug.

The present invention further provides similar peptides designed for the other amyloidogenic peptides such as AA, AL, and IAPP. In fact, the present invention also provides a peptide for inhibiting amyloidosis and/or for cytoprotection. The peptide has a sequence taken from the β-sheet region of an amyloid protein. Such peptide or a composition containing such peptide can be used for inhibiting amyloidosis and/or for cytoprotection. Alternatively, such peptide or a composition containing such peptide can be used for the manufacture of a medicament for inhibiting amyloidosis and/or for cytoprotection.

Accordingly, the present invention also provides a composition for inhibiting amyloidosis and/or for cytoprotection, which comprises a therapeutically effective amount of a peptide as defined previously in association with a pharmaceutically acceptable carrier.

In accordance with the present invention, the amyloidosis disorder includes, without limitation, prion protein related disorders, type II diabetes and Alzheimer's disease.

With regard to another aspect of the invention, diseases caused by the death or malfunctioning of a particular type or types of cells can be treated by transplanting into the patient healthy cells of the relevant type of cell. Often these cells are cultured in vitro prior to transplantation to increase their numbers, to allow them to recover after the isolation procedure or to reduce their immunogenicity. However, in many instances the transplants are unsuccessful, due to the death of the transplanted cells. The inventors have now also found that culturing of cells can lead to the formation of fibrils from endogenous proteins. Such fibrils are likely to continue to grow after the cells are transplanted and cause death or dysfunction of the cells. The inventors have also found that the peptide of the present invention or the antifibrillogenic compound of the present invention can be used to reduce the formation of fibrils.

Thus the invention also provides a process for the preparation of cells suitable for transplantation into a mammal, which cells are capable of forming fibrils. The process comprises contacting the cells with the peptide of the present invention or the antifibrillogenic compound of the present invention.

The peptide of Formula I or the antifibrillogenic compound causes breakdown of amyloid deposits which have been formed by the cells prior to the contact. Preferably, the cells are cultured in the presence of the peptide of Formula I or the antifibrillogenic compound.

For the purpose of the present invention the following expressions and terms are defined below.

The term "agents having stereoselective antifibrillogenic activity" is intended to mean any peptides, peptide analogues, peptide derivatives, or peptidomimetics which retain the stereoselective antifibrillogenic activity, the cytoprotective and anti-inflammatory activity and/or the ability to alter a natural amyloidotic protein aggregation as described herein. Peptide analogues, peptide derivatives, or peptidomimetics include any molecules that mimic the chemical structure of a peptide and retain the functional properties of the peptide (Williams, W. V. and Weiner, D. B., eds., Biologically Active Peptides: Design, Synthesis, and Utilization, vol. 1, Technomic Publishing Company Inc., Lancaster, Pa., 1993, pages 35–3 . . . ). Examples of peptide analogues, peptide derivatives, or peptidomimetics include compounds with sulfonamide, phosphoramide or non-amide linkages.

The expression "antifibrillogenic activity" is intended to mean the ability to block or prevent an amyloidogenic protein from forming fibrils, preferably by preventing it from adopting its β-pleated conformation.

The term "cytoprotection" or "cytoprotective activity" is intended to mean the ability to protect cells from amyloid-induced toxicity.

The expression "anti-inflammatory" is intended to mean the ability to block or reduce the Aβ-induced microglial activation process or to block the chemokine-induced inflammatory reaction.

The expression "retro isomer" is intended to mean a reversal of the direction of the peptide backbone.

The expression "inverso isomer" is intended to mean an inversion of the amino acid chirality used to make the peptide.

The expression "retro-inverso isomer" is intended to mean a reversal of both the peptide backbone direction and the amino acid chirality.

Except as otherwise expressly defined herein, the abbreviations used herein for designating the amino acids and the protective groups are based on recommendations of the IUPAC-IUB Commission on Biochemical Nomenclature (*Biochemistry*, 1972, 11:1726–1732).

Also, unless specified otherwise, the Aβ(1–40) is the naturally occurring Aβ (1–40), that is the all [L]-isomer.

DETAILED DESCRIPTION OF THE INVENTION

Figure 1:
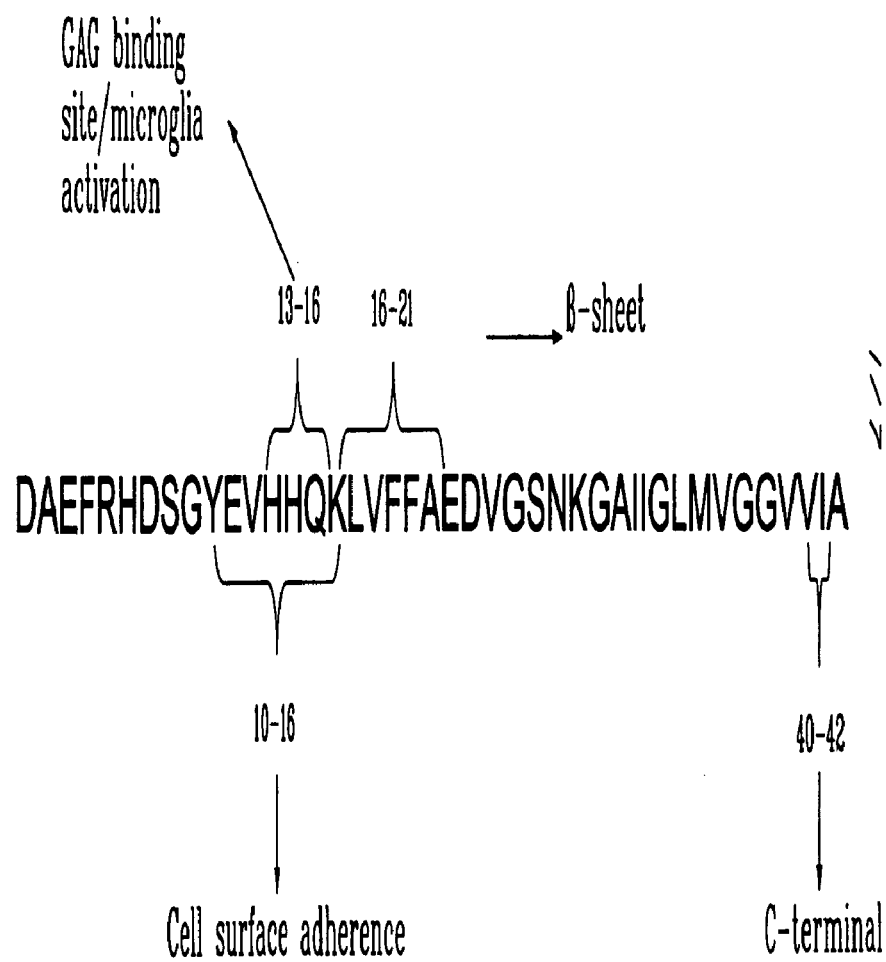
FIG. 1 illustrates the targeted sites of the protein—protein interactions required for self-assembly into β-sheet fibrils.

As illustrated in FIG. 1, internal regions of the Aβ sequence have been shown to confer characteristics of the amyloid protein. Indeed, the region between amino acid 13–16 (His-His-Gln-Lys, SEQ ID NO:23) of the amyloid protein is responsible for the interaction between the Aβ protein and the glycosaminoglycan moiety of the proteoglycans (Kisilevsky, R., et al., Proteoglycans and amyloid fibrillogenesis: The nature and origin of amyloid fibrils, Wiley, Chichester (*CIBA Foundation Symposium* 1997), pp. 58–72). Proteoglycans are known to promote amyloid fibril formation as well as protect these fibrils from proteolysis (Gupta-Bansal, R., et al., 1995, *The Journal of Biological Chemistry*, 270:18666–18671). More recently, the same region has been determined to play a role in the activation process of microglial cells by Aβ (Giulian, D., et al., 1998, *The Journal of Biological Chemistry*, 273 (45):29719–29726). This 13–16 region of Aβ, often referred to as the GAG binding site, is also part of a larger domain, the 10–16 region of the protein which has been suggested as the region responsible for the adherence of Aβ to the cell surface (Giulian, D., et al., 1996, *The Journal of Neuroscience*, 16(19):6021–6037). Such adherence of Aβ to the cell surface will allow the interaction of Aβ with the specific cells leading to either microglia activation or toxicity of neuronal cells.

These two overlapping regions of the Aβ protein, i.e. amino acids 13–16 and 10–16 are adjacent to the 16–21 region of Aβ, a short hydrophobic stretch critical for the formation of fibrillar structures (Hilbrich, C., et al., 1992, *J. Mol. Biol.*, 228:460–473). By having peptides capable of interacting with these overlapping regions of Aβ, one can aim at preventing both Aβ fibril formation and Aβ cellular interaction (i.e. microglia activation, neurotoxicity).

A preferred embodiment of the present invention is novel and arises from the unexpected finding that the all-[D] stereoisomer peptides, Lys-Lys-Leu-Val-Phe-Phe-Ala (SEQ ID NO:2) and Lys-Leu-Val-Phe-Phe-Ala (SEQ ID NO:3), are much more potent inhibitors of Aβ(1–40) fibrillogenesis then the corresponding all-[L] peptides. The all-[D] stereoisomer peptides, Lys-Lys-Leu-Val-Phe-Phe-Ala (SEQ ID NO:2) and Lys-Leu-Val-Phe-Phe-Ala (SEQ ID NO:3) are also potent cytoprotective agents.

This finding was unforeseen particularly because the researchers who originally reported peptides containing the sequence Lys-Leu-Val-Phe-Phe-Ala (SEQ ID NO:3) as an inhibitor of fibrillogenesis, state in a second article which they published: "A peptide entirely composed of amino acids in D configuration with the sequence klvff (lowercase marks amino acids in D configuration) was synthesized using the SPOT technique and assayed for $^{125}$I-LBMP1620 binding. This peptide failed to bind $^{125}$I-LBMP1620 indicating that KLVFF—KLVFF interaction is sterospecific." Tjernberg, L. O. et al. (1997) Controlling Amyloid β-Peptide Fibril Formation with Protease-stable Ligands, *J. Biol. Chem.*, 272:12602.

Inhibition of Amyloidosis

The experimental work performed leading to this invention included comparing the ability of the [D] and [L] stereoisomers of peptide Lys-Lys-Leu-Val-Phe-Phe-Ala (SEQ ID NO:2) to inhibit the fibrillogenesis process observed with the amyloidogenic peptide Aβ (1–40) in a thioflavin T fluorescence assay.

The thioflavin T fluorescence assay for fibrillogenesis is based on the principle that the fluorescent dye, thioflavin T, binds specifically to fibrillar, but not to unaggregated Aβ peptide (LeVine III, H., 1993, *Protein Science* 2:404–410). Upon binding, thioflavin T develops a characteristic fluorescence (Naiki, H., et al., 1996, *Lab. Invest.* 74: 374–383) which can be easily detected. The dye is believed to interact with the stacked cross-β pleated sheets, the common structural motif of all amyloids (LeVine III, H., 1995, *Amyloid: Int. J. Exp. Clin Invest.* 2:1.6). Thioflavin T is widely used to assay the effect of compounds on Aβ peptide fibrillogenesis (Bronfman, P. C., et al., 1995, *Neuroscience Lett.* 218:201–203).

In this assay test compounds are incubated with a solution of Aβ(1–40) (20 μM) containing 10 μM thioflavin T, in 0.02M Tris/0.02M acetate/0.15M NaCl/0.005% azide/pH 7.40 at 37° C. in sealed 384 well microplates. Readings (ex 430 nm/em 485 nm) are taken at various time intervals with a microplate fluorescence reader. An increase in fluorescence signifies the appearance of amyloid or intermediates in the production of amyloid. Inhibitors of fibrillogenesis will lead to less fluorescence production.

The results illustrated in Table 1 below, are based on the fluorescence production in the presence of test peptides at either 20 μM or 80 μM concentration, at the time intervals of 5, 19, 45, 67, 77 and 90 hours, compared to a control, buffer alone, without added inhibitory peptide.

TABLE 1

Order Of Potency of Peptide Inhibitors

| | Tested at 20 μM | Tested at 80 μM |
|---|---|---|
| (strongest activity) | 1 (D) KIVFFA | 1 (D) AFFVLK |
| | 2 (D) KKLVFFA | 1 (D) KKLVFFA |
| | 3 (D) KLVFFA | 1 (D) KLVFFA |
| | 4 (D) KFVFFA | 1 (D) KFVFFA |
| | 5 (D) AFFVLK | 5 (D) KIVFFA |
| | 6 (D) KLVF | 6 (D) KAVFFA |
| | 7 (D) KAVFFA | 7 (L) KKLVFFA |
| | 8 (L) KLVFFA | 8 (L) KLVFFA |
| | 9 (D) KLVFF | 9 (D) KLVF |
| | 10 (L) KKLVFFA | 10 (D) KLVFF |
| (weakest activity) | 11 (L) AFFVLK | 11 (L) AFFVLK |

Protocol

Aβ peptide: Aβ (1–40) 95% purity (American Peptide Company, Inc, Sunnyvale, Cal. USA, cat. 62-0-78) is disaggregated in trifluoroacetic acid and filtered through a 0.02 μM filter, (Whatman Anotop 25 plus, 0.02 μm, Catalogue no. 6809 4102) in hexafluoroisopropanol (HFIP). Solutions of Aβ (1–40) at 600 μM in HFIP are stored at –80° C.

Assay mixture: The mixture is prepared as two solutions that are combined upon addition to the 384 well microplate (Corning Costar cat. 3705).
 i) Solution A consists of test peptides in 0.02M Tris/ 0.02M acetate/0.15M NaCl/0.01% azide at pH 7.40 or buffer alone (control),
 ii) Solution B consists of Aβ(1–40) 40 μM, thioflavin T 20 μM in 0.02M Tris/0.02M acetate/0.15M NaCl at pH 7.40. This solution is prepared by drying the Aβ peptide under nitrogen and then resuspending this in 0.04M Tris base with 15 minutes sonication. An equal volume of 0.04M acetic acid containing 0.3 M NaCl is added and the solution is adjusted to pH 7.40±0.02. A small volume of 5 mM thioflavin T is added to the solution to give a final 20 μM concentration of thioflavin T.
 iii) The microplate is loaded with 40 μL of solution A followed by 40 μL of solution B which gives a final 20 μM Aβ(1–40), 10 μM thioflavin T, and either 20 μM, 80 μM or 100 μM test compound in 0.02M Tris/0.02M acetate/0.15M NaCl/0.005% azide, pH 7.40. The plate is sealed and loaded into the microplate fluorescence reader.

Fluorescence measurement data analysis: The HTS-7000 Bio Assay Reader, Perkin Elmer, is used to perform kinetic runs of about 5 days. Readings were taken at various time intervals, 5, 19, 45, 67, 77 and 90 hours, with one minute shaking before each reading. Bandpass filters used were: excitation 430 nm, emission 485 mm.

Calculations

The rank order of efficacy of the peptides is determined by observing which peptides allow the appearance of fluorescence, above the background level, first. For example in the presence of buffer control alone, fluorescence appears earlier than when any of the peptides is present. The most active peptides prevent the appearance of fluorescence even after 90 hours of incubation.

The results achieved in the thioflavin T fibrillogenesis assays show that all-[D] stereoisomer peptide was about 60 times more potent then the all-[L] stereoisomer peptide. This is based on the observation that 400 μM all-[L] stereoisomer was required to give an equivalent inhibition to that produced with 6.1 µM all-[D] stereoisomer peptide.

The results achieved in the Aβ-NBD environmental probe fibrillogenesis assay showed that the all-[D] stereoisomer peptide was at least 30 times more potent than the all-[L] stereoisomer peptide. This estimate is based on the observation that the lowest concentration of all-[D] peptide tested (25 µM) was more potent than the highest concentration of the all-[L] peptide (800 µM).

β-Sheet and GAG Binding Domains Peptides

Novel peptides and peptidomimetics that include complementary sequences to certain portions of amyloidogenic peptides such as Aβ, AA, AL, IAPP, and prion proteins are designed to be capable of inhibition of Protein—Protein interactions or self assembly. The targeted portions in the various disease-causing proteins aforementioned, preferably contain one or more charged residues such as aspartate, glutamate, lysine, histidine and arginine. Such peptides and their peptidomimetics will inhibit fibrillogenesis of the amyloidogenic peptides and prion proteins and interfere with chemokines binding to the cell surface proteoglycans leading to dimerization or tetramerization by interacting with their GAG binding domains. In the case of Aβ, these interactions lead to cytoprotection as well as inhibition of inflammatory response and serve as potent therapeutics for the treatment of Alzheimer's disease. In the case of chemokine-related disorders these interactions may lead to a decrease in the uncontrolled inflammatory response associated with some diseases.

Other amyloidogenic peptides such as IAPP, have also been tested. For example, 2 peptides from the β-sheet region of IAPP have been shown to inhibit IAPP fibril formation using the thioflavin T fluorescence assay, circular dichroism (measures secondary structure) and the electron microscope (to look at fibrils directly).

The full-length IAPP is 37 amino acids and the β-sheet region is the 20–29 sequence. The 20–29 sequence is critical for forming β-sheet and has been previously shown to be a key region in modulating IAPP aggregation and folding. Hexapeptides from this β-sheet region were examined and 2 were found to be active.

Hexapeptides spanning the 20–29 region (Ser-Asn-Asn-Phe-Gly-Ala-Ile-Leu-Ser-Ser) of the IAPP protein were synthesized and tested for their ability to prevent fibril formation as determined by circular dichroism and the thioflavin T assay. Hexapeptides were designed and were found to be capable of blocking the formation of IAPP fibrils. These peptides (Ser-Asn-Asn-Phe-Gly-Ala- and Asn-Asn-Phe-Gly-Ala-Ile) were directed towards the central core of the 20–29 region.

Novel peptides containing 3–6 residues that are complementary (in terms of their charges) to the 10–16 segment of Aβ peptide have been shown for the first time to strongly interact with Aβ peptide. They provide a starting point for the design of BBB (blood brain barrier) permeable peptidomimetics. In principle, the present invention provides similar peptides can be designed for the other amyloidogenic peptides such as AA, AL, and IAPP.

Asp-Asp-Asp (SEQ ID NO:21), a tripeptide, when incubated with Aβ40 under physiological conditions shows a slight decrease at time t=0 in the amount of β-sheet content as is evident by the CD spectrum. Incubation of this tripeptide with Aβ40 for 24 hours shows no trace of β-sheet conformation of the Aβ40 and clearly indicates the ability of this tripeptide to strongly interact with Aβ 40 peptide and keep Aβ40 in a randomized and non-fibrillary conformation.

The anti-fibrillogenic property of this tripeptide is also supported by the Aβ 42 solubilization assay.

Lys-Val-Asp-Asp-Gln-Asp (SEQ ID NO:22), a hexapeptide, when incubated with Aβ 40 under physiological conditions shows an increase at time t=0 in the amount of β-sheet content as is evident by the CD spectrum. Incubation of this hexapeptide with Aβ40 for 24 hours shows a dramatic increase in β-sheet content of the Aβ40 and clearly indicates the ability of this hexapeptide to strongly interact with Aβ 40 peptide and organize it into a β-sheet conformation. Electron microscopy of the mixture failed to show any fibrils indicating that this particular compound is in fact an anti-fibrillogenic compound with regard to Aβ. In vitro results with NBD and thioflavin-T based fluorescence assays confirm this finding. It is the understanding of the inventors that this interesting observation will lead to a greater understanding of fibrillogenesis of Aβ40 and Aβ42 peptides and as a result, will provide important information for the design of potent anti-fibrillogenic compounds for Aβ, other amyloidotic peptides such as AA, AL and IAPP for the treatment of diseases such as Alzheimer's, Type II Diabetes and amyloidosis related disorders. The same principle can also be applied to the design of peptide type compounds for the inhibition of binding of various chemokines to the cell surface as well as inhibition of self assembly and cellular adherence of prion proteins.

Figure 2:
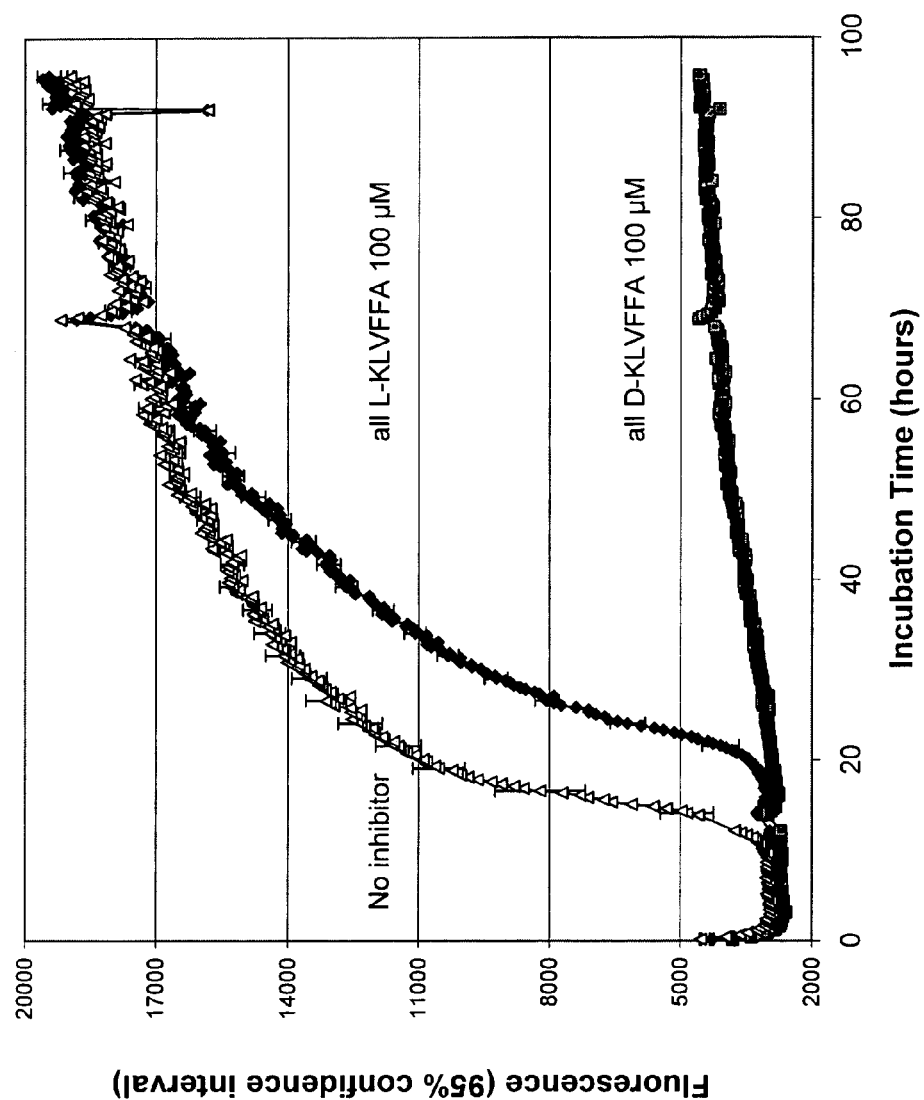
FIG. 2 illustrates the result of a thioflavin T fluorescence assay for fibril formation by [L]-Aβ (1–40) in the absence and presence of a peptide in accordance with one embodiment of the invention.

The results illustrated in FIG. 2 show that all [D]-Lys-Leu-Val-Phe-Phe-Ala (SEQ. ID NO: 3) is a more potent inhibitor of Aβ (1–40) assembly in the thioflavin T fluorescence assay than is all [L]-Lys-Leu-Val-Phe-Phe-Ala. Since the naturally occurring Aβ (1–40) used in these experiments was the all-[L] amino acid version, these results indicate that an inhibitor peptide works best when containing amino acids of the opposite chirality.

Figure 3:
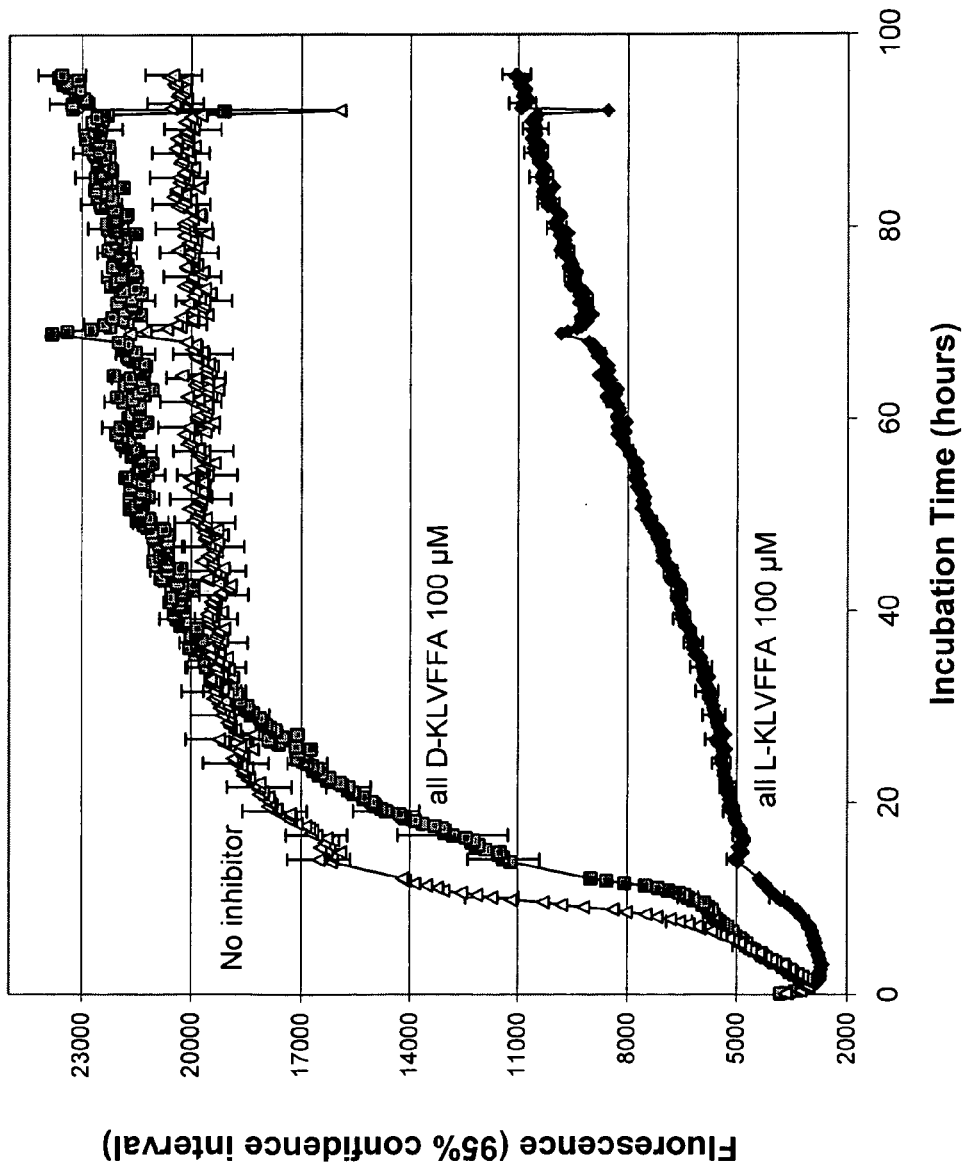
FIG. 3 shows the result of the same assay as in FIG. 2 for fibril formation by [D]-Aβ (1–40)

FIG. 3 demonstrates that the same rule of opposite chirality illustrated in FIG. 2 applies for the assembly of Aβ (1–40) synthesized using amino acids of the [D] type. In this experiment all-[L]-Lys-Leu-Val-Phe-Phe-Ala (SEQ. ID NO:3) is a more potent inhibitor in the all-[D]-Aβ (1–40) assembly reaction than all-[D]-Lys-Leu-Val-Phe-Phe-Ala. This result confirms that peptides of opposite chirality are better inhibitors.

Figure 4:
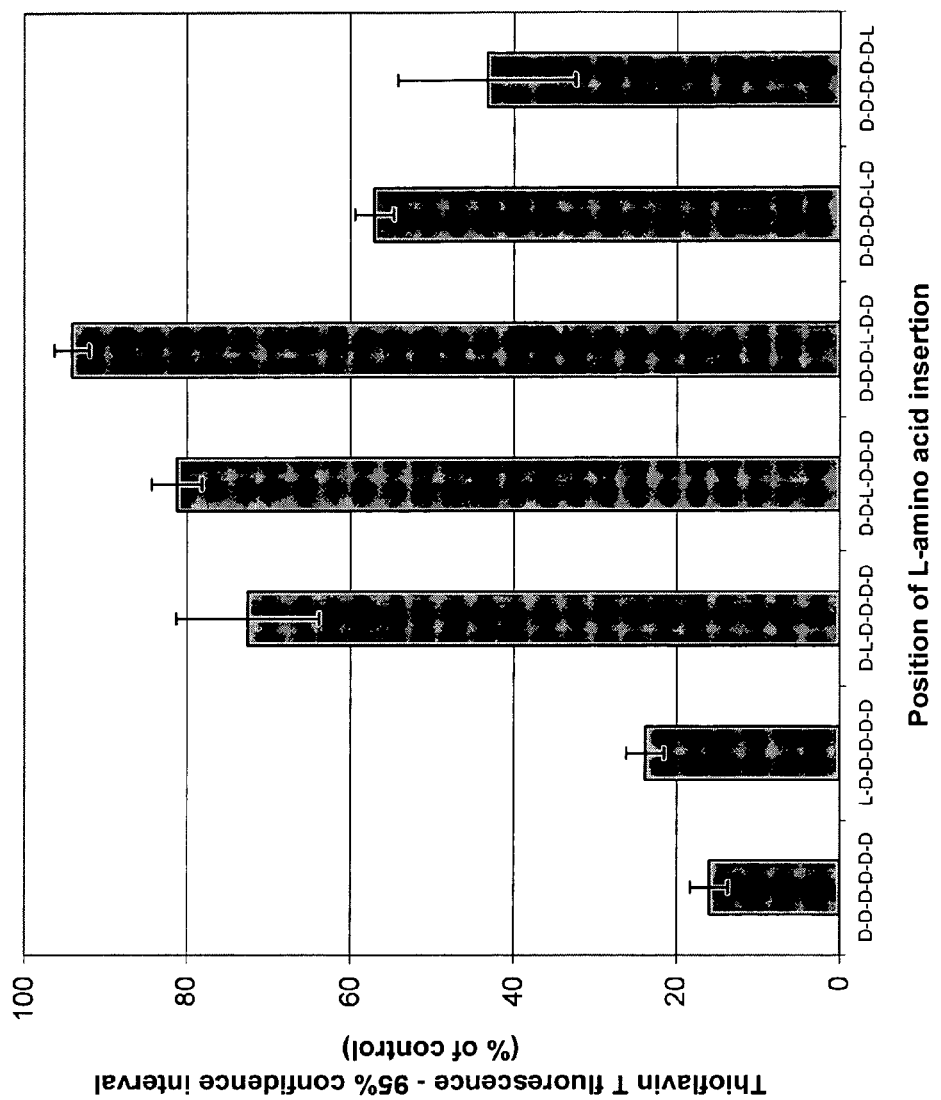
FIG. 4 is a bar graph illustrating the percentage of thioflavin T fluorescence in the presence of the [D]-peptide used in FIG. 2, with or without single substitutions of corresponding [L]-amino acids.

FIG. 4 illustrates the inhibition of Aβ (1–40) fibril formation by all-[D]-Lys-Leu-Val-Phe-Phe-Ala (20 µM) with or without single substitutions of [L]-amino acids in the thioflavin T fluorescence assay. In this experiment the ability of the all-[D]-Lys-Leu-Val-Phe-Phe-Ala peptide to inhibit Aβ (1–40) fibril formation, measured as percentage of thioflavin T fluorescence in the absence of peptide (control), was compared to [D]-Lys-Leu-Val-Phe-Phe-Ala peptides with single [L]-amino acid replacements. None of the mixed chirality Lys-Leu-Val-Phe-Phe-Ala peptides were more potent than the original all-[D] peptide. This result demonstrates that [D]-amino acids are more potent inhibitors of Aβ (1–40) fibrillogenesis than [L]-amino acids.

However as seen in FIG. 4 some peptides with single [L] substitutions do retain inhibitory activity. In particular peptides in which the [D] isomer of the Lys, the second Phe and the Ala are substituted with the [L]-isomers retain inhibitory activity. The substitutions, which reduce inhibitory activity the most, are the Leu, the Val and the first Phe, indicating that these residues contribute the most to the potency of the [D]-peptide. From FIG. 4, it is apparent that peptides with mixed chirality or with at least one [D]-substituted amino acid are also inhibitors, although not as potent as the all-[D] peptide. These mixed-chirality peptides are thus meant to be included in the present invention.

Figure 5:
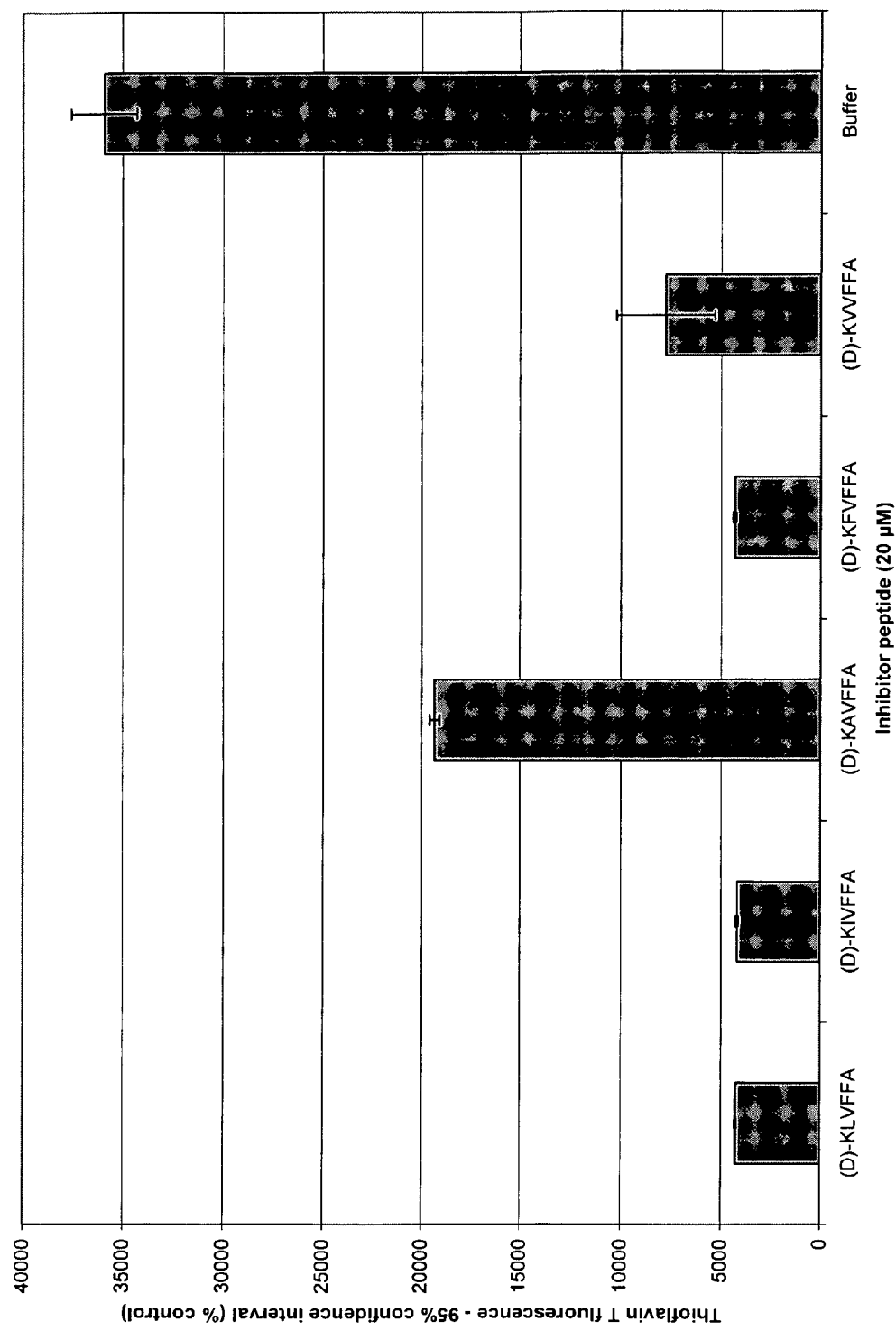
FIG. 5 is a bar graph illustrating a thioflavin T fluorescence assay for fibril formation by [L]-Aβ (1–40) in the presence of the [D]-peptide used in FIG. 2, with or without substitution of the Leu residue by other hydrophobic amino acids.

FIG. 5 illustrates the inhibition of Aβ (1–40) fibril formation in the thioflavin T fluorescence assay by all-[D]-Lys-Leu-Val-Phe-Phe-Ala (20 μM), with or without replacement of the leucine by other hydrophobic amino acids. In this experiment all the peptides tested retained some inhibitory activity. This result demonstrates that the leucine residue is not critical for inhibition of Aβ fibril formation in the all-[D] peptide. These results illustrated in FIG. 5 were non-obvious and unexpected in light of a prior publication which identified the Leucine residue as critical in an all-[L] version of the peptide (Tjernberg L O et al., *J. Biol. Chem.* 271:8545, 1996).

Cytoprotection

The experimental work performed leading to this invention also included comparing the ability of [D] and [L] stereoisomers of the peptides of the present invention to show cytoprotective activity, i.e. to protect cells from Aβ toxicity.

Figure 6:
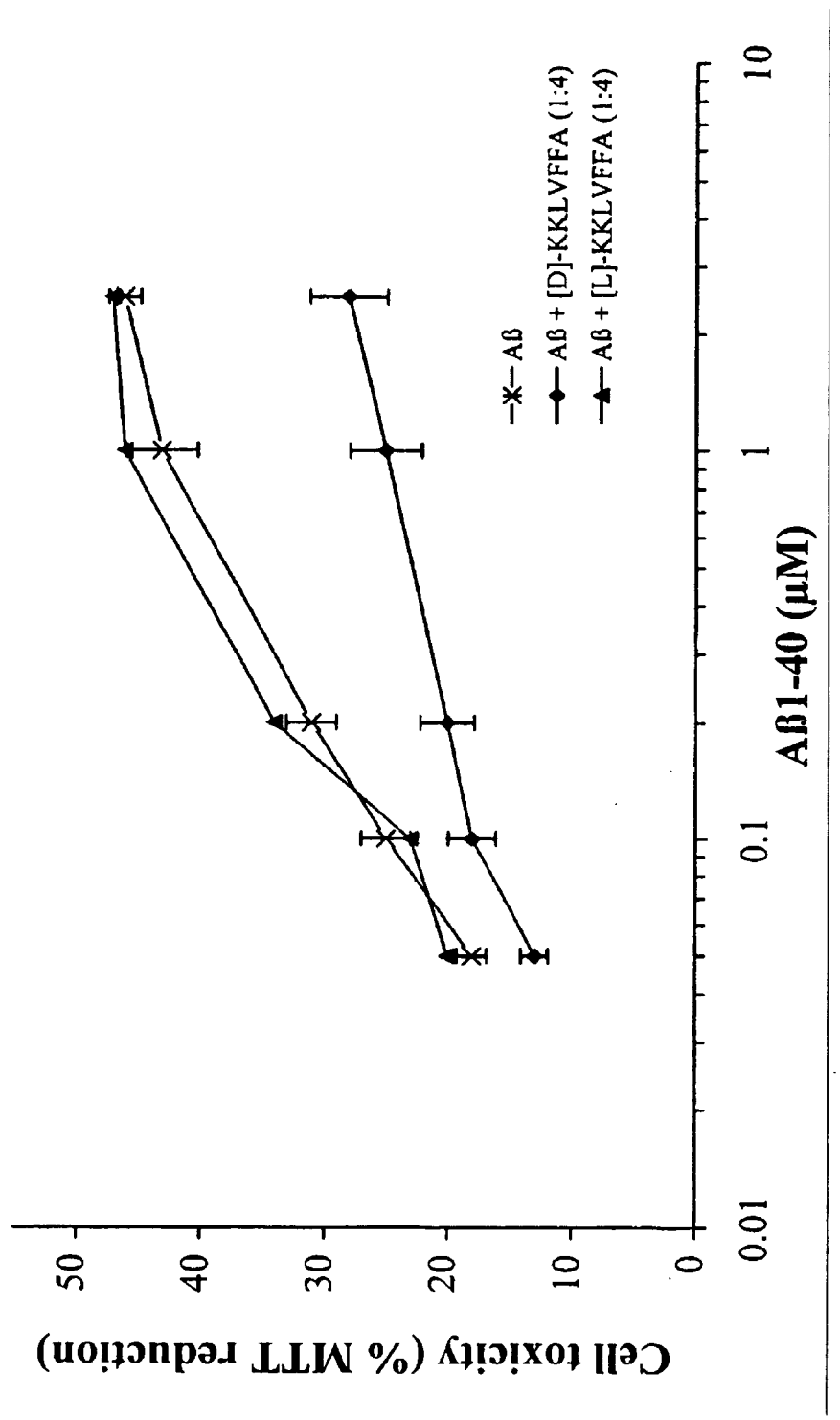
FIG. 6 illustrates the toxicity of [L]-Aβ (1–40) in the absence and presence of peptides in accordance with one embodiment of the invention.

FIG. 6 uses the MTT assay on SH-SY5Y cells.

Protocol

A SH-SY5Y human neuroblast cell line (American Type Culture Collection, cat. CRL-2266) is cultured according to technical specifications. Monomerized Aβ (1–40) is prepared using trifluoroacetic acid and hexafluoroisopropanol, in the same way already described for the thioflavin T fluorescence assay. Monomerized Aβ at various concentrations in TANA buffer (0.02 M TRIS base pH 7.4, 0.02M acetate, 0.15 M NaCl) is added to 100 μM test peptide and the mixture is incubated for 24 hours at 37° C. with agitation, in order to allow polymerization to occur. Cells are adhered to a 96-well microplate for 2 hours at 37° C. and 5% $CO_2$ before the Aβ-peptide mixture, or buffer alone (control), is added. The microplate is gently agitated and incubated for 20–24 hours at 37° C. and 5% $CO_2$. Cell viability is determined by a MTT-based colorimetric assay. The MTT assay (Boehringer Mannheim, Cell Proliferation Kit 1) is based on the principle that the yellow tetrazolium salt MTT is cleaved in metabolically-active cells to produce purple formazan crystals. The formazan crystals are solubilized and the resulting colored solution is quantified using a scanning multiwell spectrophotometer (ELISA reader, Absorbance $A_{560}$ nm). Cellular toxicity was calculated as follows:

$$\text{Toxicity (\%)} = 100 - \frac{(O.D. \text{ sample} - O.D. \text{ Blank})}{(O.D. \text{ Control} - O.D. \text{ Blank})}.$$

FIG. 6 shows the neurotoxicity of Aβ (1–40) in the absence or presence of various peptides of the present invention. In this experiment the all-[D]-Lys-Lys-Leu-Val-Phe-Phe-Ala (SEQ. ID NO: 2) peptide is a more potent inhibitor of Aβ neurotoxicity than the all-[L]-Lys-Lys-Leu-Val-Phe-Phe-Ala peptide in the cytoprotection assay.

Figure 7:
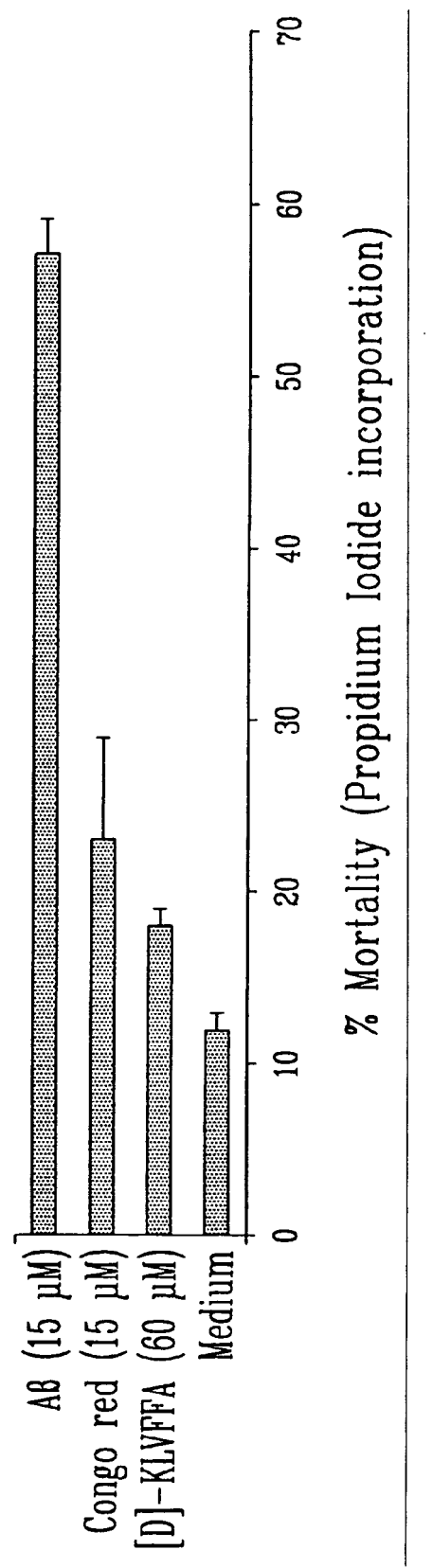
FIG. 7 is a bar graph illustrating the toxicity of [L]-Aβ (1–40) in the presence of another peptide of the present invention.

FIG. 7 uses the propidium iodide assay on primary cortical neurons. Briefly, fetal rat primary cortical neurons are isolated and cultured according to Durkin, J. P. et al., J. Neurochem., 66:951–962, 1996. Neurons are plated in a 48 well microplate. 7 days after plating the neuronal culture media is supplemented with B27 (Life Technologies, Data sheet form No. 3755). A mixture of Aβ and test peptide is added to the cortical neurons for 3 days at 37° C. and 5% CO2.

Cell viability is then visually assessed as the proportion of phase-bright cells that exclude propidium iodide, since only dead cells take up propidium iodide.

FIG. 7 shows the potent cytoprotective activity of all-[D]-Lys-Leu-Val-Phe-Phe-Ala (SEQ ID NO:3). This experiment shows the potent cytoprotective activity of all-[D]-Lys-Leu-Val-Phe-Phe-Ala compared to Congo red, which is a known cytoprotective agent and compared to the absence of any cytoprotective agent (Aβ alone).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. An antifibrillogenic agent for inhibiting amyloidosis and/or for cytoprotection, which comprises a peptide of Formula I consisting of all [D]-amino acids, or a retro-isomer of a peptide of Formula I consisting of all [D]-amino acids, wherein said peptide of Formula I is selected from the group consisting of:

| | |
|---|---|
| Lys-Ile-Val-Phe-Phe-Ala | (SEQ ID NO:1); |
| Lys-Lys-Leu-Val-Phe-Phe-Ala | (SEQ ID NO:2); |
| Lys-Phe-Val-Phe-Phe-Ala | (SEQ ID NO:4); |
| Lys-Ala-Val-Phe-Phe-Ala | (SEQ ID NO:7); |
| Lys-Val-Val-Phe-Phe-Ala | (SEQ ID NO:9); |
| Lys-Ile-Val-Phe-Phe-Ala-NH$_2$ | (SEQ ID NO:10); |
| Lys-Phe-Val-Phe-Phe-Ala-NH$_2$ | (SEQ ID NO:12); |
| Lys-Ala-Val-Phe-Phe-Ala-NH$_2$ | (SEQ ID NO:15); |
| Lys-Val-Val-Phe-Phe-Ala-NH$_2$ | (SEQ ID NO:17); |
| Lys-Leu-Val-Phe-Phe-Ala-Gln | (SEQ ID NO:18); and |
| Lys-Leu-Val-Phe-Phe-Ala-Gln-NH$_2$ | (SEQ ID NO:19). |

2. An antifibrillogenic agent for inhibiting amyloidosis and/or for cytoprotection, which comprises a peptide consisting of all [D]-amino acids, or a retro-isomer of a peptide consisting of all [D]-amino acids, wherein said peptide is a peptide of SEQ ID NO:2.

3. A composition for the treatment of amyloidosis disorders in a patient, which comprises a therapeutically effective amount of a peptide of claim 1 or a retro-isomer thereof, and a pharmaceutically acceptable carrier.

4. The composition of claim 3, wherein said amyloidosis disorder is Alzheimer's disease.

5. A composition for the treatment of amyloidosis disorders in a patient, which comprises a therapeutically effective amount of an antifibrillogenic agent as defined in claim 1, and a pharmaceutically acceptable carrier.

6. The composition of claim 5, wherein said amyloidosis disorder is Alzheimer's disease.

7. A composition for inhibiting amyloidosis and/or for cytoprotection, which comprises a therapeutically effective amount of a peptide as defined in claim 1 or a retro-isomer thereof, and a pharmaceutically acceptable carrier.

8. An antifibrillogenic agent for inhibiting amyloidosis and/or for cytoprotection, which comprises a peptide selected from the group consisting of:

| | |
|---|---|
| Lys-Ile-Val-Phe-Phe-Ala | (SEQ ID NO:1); |
| Lys-Lys-Leu-Val-Phe-Phe-Ala | (SEQ ID NO:2); |
| Lys-Phe-Val-Phe-Phe-Ala | (SEQ ID NO:4); |
| Lys-Ala-Val-Phe-Phe-Ala | (SEQ ID NO:7); |
| Lys-Val-Val-Phe-Phe-Ala | (SEQ ID NO:9); |
| Lys-Ile-Val-Phe-Phe-Ala-NH$_2$ | (SEQ ID NO:10); |
| Lys-Phe-Val-Phe-Phe-Ala-NH$_2$ | (SEQ ID NO:12); |
| Lys-Ala-Val-Phe-Phe-Ala-NH$_2$ | (SEQ ID NO:15); |
| Lys-Val-Val-Phe-Phe-Ala-NH$_2$ | (SEQ ID NO:17); |
| Lys-Leu-Val-Phe-Phe-Ala-Gln | (SEQ ID NO:18); and |
| Lys-Leu-Val-Phe-Phe-Ala-Gln-NH$_2$ | (SEQ ID NO:19); | wherein said amino acid sequence consists of all [D]-amino acids.

9. An antifibrillogenic agent for inhibiting amyloidosis and/or for cytoprotection, which comprises the sequence of SEQ ID NO:2, wherein said amino acid sequence consists of all [D]-amino acids.

10. A composition for the treatment of amyloidosis disorders in a patient, which comprises a therapeutically effective amount of an antifibrillogenic agent comprising the amino acid sequence of SEQ ID NO:2 wherein said sequence consists of all [D]-amino acids, and a pharmaceutically acceptable carrier.

11. A composition for the treatment of Alzheimer's disease in a patient, which comprises a therapeutically effective amount of an antifibrillogenic agent comprising the amino acid sequence of SEQ ID NO:2 wherein said sequence consists of all [D]-amino acids, and a pharmaceutically acceptable carrier.

12. An antifibrillogenic agent for inhibiting amyloidosis and/or for cytoprotection, which comprises the amino acid sequence of SEQ ID NO:1, wherein said sequence consists of all [D]-amino acids.

13. An antifibrillogenic agent for inhibiting amyloidosis and/or for cytoprotection, which comprises the amino acid sequence of SEQ ID NO:4, wherein said sequence consists of all [D]-amino acids.

14. An antifibrillogenic agent for inhibiting amyloidosis and/or for cytoprotection, which comprises the amino acid sequence of SEQ ID NO:7, wherein said sequence consists of all [D]-amino acids.

15. An antifibrillogenic agent for inhibiting amyloidosis and/or for cytoprotection, which comprises the amino acid sequence of SEQ ID NO:9, wherein said sequence consists of all [D]-amino acids.

16. An antifibrillogenic agent for inhibiting amyloidosis and/or for cytoprotection, which comprises the amino acid sequence of SEQ ID NO:10, wherein said sequence consists of all [D]-amino acids.

17. An antifibrillogenic agent for inhibiting amyloidosis and/or for cytoprotection, which comprises the amino acid sequence of SEQ ID NO:12, wherein said sequence consists of all [D]-amino acids.

18. An antifibrillogenic agent for inhibiting amyloidosis and/or for cytoprotection, which comprises the amino acid sequence of SEQ ID NO:15, wherein said sequence consists of all [D]-amino acids.

19. An antifibrillogenic agent for inhibiting amyloidosis and/or for cytoprotection, which comprises the amino acid sequence of SEQ ID NO:17, wherein said sequence consists of all [D]-amino acids.

20. An antifibrillogenic agent for inhibiting amyloidosis and/or for cytoprotection, which comprises the amino acid sequence of SEQ ID NO:18, wherein said sequence consists of all [D]-amino acids.

21. An antifibrillogenic agent for inhibiting amyloidosis and/or for cytoprotection, which comprises the amino acid sequence of SEQ ID NO:19, wherein said sequence consists of all [D]-amino acids.

* * * * *

UNITED STATES PATENT AND TRADEMARK OFFICE
CERTIFICATE OF CORRECTION

PATENT NO. : 7,060,670 B1
APPLICATION NO. : 10/009122
DATED : June 13, 2006
INVENTOR(S) : Chalifour et al.

It is certified that error appears in the above-identified patent and that said Letters Patent is hereby corrected as shown below:

Column 7, Line 26, replace "sterospecific" with
--stereospecific--.

Signed and Sealed this

Twenty-sixth Day of December, 2006

JON W. DUDAS
*Director of the United States Patent and Trademark Office*

SEQUENCE LISTING

```
<160> NUMBER OF SEQ ID NOS: 24

<210> SEQ ID NO 1
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 1

Lys Ile Val Phe Phe Ala
 1               5

<210> SEQ ID NO 2
<211> LENGTH: 7
<212> TYPE: PRT
<213> ORGANISM: Artificial Sequence
<220> FEATURE:
```

```
<223> OTHER INFORMATION: peptide having antifibrillogenic activity
      and/or neuroprotection

<400> SEQUENCE: 2

Lys Lys Leu Val Phe Phe Ala
 1               5

<210> SEQ ID NO 3
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 3

Lys Leu Val Phe Phe Ala
 1               5

<210> SEQ ID NO 4
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 4

Lys Phe Val Phe Phe Ala
 1               5

<210> SEQ ID NO 5
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 5

Ala Phe Phe Val Leu Lys
 1               5

<210> SEQ ID NO 6
<211> LENGTH: 4
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 6

Lys Leu Val Phe
 1

<210> SEQ ID NO 7
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 7

Lys Ala Val Phe Phe Ala
 1               5
```

```
<210> SEQ ID NO 8
<211> LENGTH: 5
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 8

Lys Leu Val Phe Phe
 1               5

<210> SEQ ID NO 9
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 9

Lys Val Val Phe Phe Ala
 1               5

<210> SEQ ID NO 10
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (6)...(6)

<400> SEQUENCE: 10

Lys Ile Val Phe Phe Ala
 1               5

<210> SEQ ID NO 11
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (6)...(6)

<400> SEQUENCE: 11

Lys Leu Val Phe Phe Ala
 1               5

<210> SEQ ID NO 12
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (6)...(6)

<400> SEQUENCE: 12

Lys Phe Val Phe Phe Ala
 1               5

<210> SEQ ID NO 13
<211> LENGTH: 6
<212> TYPE: PRT
```

```
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (6)...(6)

<400> SEQUENCE: 13

Ala Phe Phe Val Leu Lys
 1               5

<210> SEQ ID NO 14
<211> LENGTH: 4
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (4)...(4)

<400> SEQUENCE: 14

Lys Leu Val Phe
 1

<210> SEQ ID NO 15
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (6)...(6)

<400> SEQUENCE: 15

Lys Ala Val Phe Phe Ala
 1               5

<210> SEQ ID NO 16
<211> LENGTH: 5
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (5)...(5)

<400> SEQUENCE: 16

Lys Leu Val Phe Phe
 1               5

<210> SEQ ID NO 17
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (6)...(6)

<400> SEQUENCE: 17

Lys Val Val Phe Phe Ala
 1               5

<210> SEQ ID NO 18
<211> LENGTH: 7
```

```
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 18

Lys Leu Val Phe Phe Ala Gln
1               5

<210> SEQ ID NO 19
<211> LENGTH: 7
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (7)...(7)

<400> SEQUENCE: 19

Lys Leu Val Phe Phe Ala Gln
1               5

<210> SEQ ID NO 20
<211> LENGTH: 9
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (9)...(9)

<400> SEQUENCE: 20

His His Gln Lys Leu Val Phe Phe Ala
1               5

<210> SEQ ID NO 21
<211> LENGTH: 3
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 21

Asp Asp Asp
1

<210> SEQ ID NO 22
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection

<400> SEQUENCE: 22

Lys Val Asp Asp Gln Asp
1               5

<210> SEQ ID NO 23
<211> LENGTH: 4
<212> TYPE: PRT
<213> ORGANISM: Artificial Sequence
<220> FEATURE:
<223> OTHER INFORMATION: peptide having antifibrillogenic activity
      and/or neuroprotection
```

```
-continued

<400> SEQUENCE: 23

His His Gln Lys
 1

<210> SEQ ID NO 24
<211> LENGTH: 6
<212> TYPE: PRT
<213> ORGANISM: Artificial Sequence
<220> FEATURE:
<223> OTHER INFORMATION: peptide having antifibrillogenic activity
      and/or neuroprotection
<221> NAME/KEY: AMIDATION
<222> LOCATION: (6)...(6)

<400> SEQUENCE: 24

Gln Lys Leu Val Phe Phe
 1               5
```